US010489725B2

(12) United States Patent
Jensen et al.

(10) Patent No.: US 10,489,725 B2
(45) Date of Patent: Nov. 26, 2019

(54) SYSTEMS AND METHODS FOR CONTROLLING BUSINESS PROCESSES THROUGH INFORMATION TECHNOLOGY OPERATIONAL CONTROLS

(71) Applicant: Aetna Inc., Hartford, CT (US)

(72) Inventors: Claus T. Jensen, Pawling, NY (US); Robert Samuel, Blue Bell, PA (US); Gerald Cormier, East Longmeadow, MA (US); David Fitzgerald, Glenmoore, PA (US)

(73) Assignee: Aetna Inc., Hartford, CT (US)

( * ) Notice: Subject to any disclaimer, the term of this patent is extended or adjusted under 35 U.S.C. 154(b) by 428 days.

(21) Appl. No.: 15/390,907

(22) Filed: Dec. 27, 2016

(65) Prior Publication Data

US 2018/0018599 A1    Jan. 18, 2018

Related U.S. Application Data

(60) Provisional application No. 62/363,454, filed on Jul. 18, 2016.

(51) Int. Cl.
*G06Q 10/06* (2012.01)
*G16H 10/60* (2018.01)
(Continued)

(52) U.S. Cl.
CPC .............. *G06Q 10/06* (2013.01); *G16H 10/40* (2018.01); *G16H 10/60* (2018.01); *G16H 40/20* (2018.01); *G16H 70/20* (2018.01)

(58) Field of Classification Search
CPC ......... G06Q 10/00–50/00; G16H 10/00–80/00
(Continued)

(56) References Cited

U.S. PATENT DOCUMENTS 6,041,306 A * 3/2000 Du .................. G06F 9/4843
705/7.26
6,718,535 B1 * 4/2004 Underwood ............ G06F 9/451
717/101
(Continued)

OTHER PUBLICATIONS

Powley, Wendy, et al. "Autonomic workload execution control using throttling." 2010 IEEE 26th International Conference on Data Engineering Workshops (ICDEW 2010). IEEE, 2010. (Year: 2010).*
(Continued)

*Primary Examiner* — Alan S Miller
(74) *Attorney, Agent, or Firm* — Leydig, Voit & Mayer, Ltd.

(57) ABSTRACT

A system and method for controlling business processes through information technology operational controls are disclosed. The method includes: receiving a business process; monitoring a load at each of multiple layers of the system; sending, to an end-to-end throttle controller, for each layer of the multiple layers, layer load data corresponding to the load at the layer, wherein each layer load data contains data related to a single layer; determining whether any adjustments should be made to throttling policies corresponding to the multiple layers based on the multiple layer load data; sending any adjustments that should be made to throttle agents of one or more layers; updating the throttling policies of one or more layers based on the adjustments; and, continuing executing the business process based on the updated throttling policies.

20 Claims, 9 Drawing Sheets

(51) Int. Cl.
*G16H 40/20* (2018.01)
*G16H 10/40* (2018.01)
*G16H 70/20* (2018.01)

(58) Field of Classification Search
USPC .............................................. 705/7.11–7.42
See application file for complete search history.

(56) References Cited

U.S. PATENT DOCUMENTS

| | | | | |
|---|---|---|---|---|
| 6,952,688 | B1* | 10/2005 | Goldman | G06N 5/022 706/45 |
| 6,983,321 | B2* | 1/2006 | Trinon | G06Q 10/06 709/224 |
| 7,080,378 | B1* | 7/2006 | Noland | G06F 9/5083 709/224 |
| 7,412,513 | B2* | 8/2008 | Levanoni | G06F 9/4881 709/225 |
| 7,426,736 | B2* | 9/2008 | Cole | G06Q 10/0635 719/318 |
| 7,565,333 | B2* | 7/2009 | Grichnik | G05B 17/02 706/12 |
| 7,774,458 | B2* | 8/2010 | Trinon | G06Q 10/06 709/224 |
| 8,276,152 | B2* | 9/2012 | Sanghvi | G06F 8/71 715/771 |
| 8,276,161 | B2* | 9/2012 | Cole | G06Q 10/0635 719/318 |
| 8,544,010 | B2* | 9/2013 | Huang | G06F 9/544 710/1 |
| 8,631,403 | B2* | 1/2014 | Soundararajan | G06F 9/5077 718/1 |
| 8,732,693 | B2* | 5/2014 | Mutisya | G06F 11/3688 717/168 |
| 8,990,812 | B2* | 3/2015 | Krishnaraj | G06F 9/5038 718/100 |
| 2002/0138571 | A1* | 9/2002 | Trinon | G06Q 10/06 709/204 |
| 2002/0174093 | A1* | 11/2002 | Casati | G06Q 30/02 |
| 2006/0059253 | A1* | 3/2006 | Goodman | G06Q 10/10 709/223 |
| 2006/0133412 | A1* | 6/2006 | Callaghan | G06F 9/54 370/465 |
| 2008/0086731 | A1* | 4/2008 | Trossman | G06F 9/50 718/100 |
| 2008/0255905 | A1* | 10/2008 | Cole | G06Q 10/0635 705/7.28 |
| 2009/0106424 | A1* | 4/2009 | Safari | G06F 11/1433 709/226 |
| 2009/0150887 | A1* | 6/2009 | Sanghvi | G06F 3/0482 718/102 |
| 2011/0125894 | A1* | 5/2011 | Anderson | H04L 9/3213 709/224 |
| 2011/0153538 | A1* | 6/2011 | Jolfaei | G06N 5/025 706/47 |
| 2012/0216243 | A1* | 8/2012 | Gill | G06F 21/55 726/1 |
| 2016/0337199 | A1* | 11/2016 | Degioanni | H04L 43/045 |
| 2017/0034036 | A1* | 2/2017 | Kohan | H04L 67/42 |

OTHER PUBLICATIONS

Kwok, Thomas, Thao Nguyen, and Linh Lam. "A software as a service with multi-tenancy support for an electronic contract management application." 2008 IEEE International Conference on Services Computing. vol. 2. IEEE, 2008. (Year: 2008).*

CA Technologies, "CA Nimsoft Monitor," Probe Guide for E2E Application Response Monitoring, Ver. 2.2, pp. 1-26 (Jun. 2014).

* cited by examiner

SYSTEMS AND METHODS FOR CONTROLLING BUSINESS PROCESSES THROUGH INFORMATION TECHNOLOGY OPERATIONAL CONTROLS

CROSS-REFERENCE TO RELATED APPLICATIONS

This application claims the benefit of U.S. Provisional Application No. 62/363,454, filed on Jul. 18, 2016, which is hereby incorporated by reference in its entirety.

TECHNICAL FIELD

Embodiments of the disclosure relate to computer processing and, more particularly, to systems and methods for controlling business processes through information technology operational controls.

BACKGROUND

Enterprise systems include servers, storage, and associated software deployed in a large scale that may serve as an information technology (IT) infrastructure for businesses, governments, or other large organizations. Enterprise systems manage large volumes of data and are designed to offer and provide high levels of transaction performance and data security. These systems are also designed to support business processes, information flows, data analytics, etc. Enterprise systems include various individual system assets or resources. Current enterprise systems may have resource or system asset bottlenecks, for example, when executing business processes. These bottlenecks may degrade overall system performance and result in inefficiently utilizing system assets.

SUMMARY

One embodiment of the disclosure provides a method for controlling business processes through information technology operational controls, the method performed by one or more servers in a system, the one or more servers including one or more processors. The method includes: receiving a business process input into the system; monitoring a load at each of multiple layers of the system; sending, to an end-to-end throttle controller, for each layer of the multiple layers, layer load data corresponding to the load at the layer, wherein each layer load data contains data related to a single layer of the multiple layers of the system; determining whether any adjustments should be made to one or more throttling policies corresponding to the multiple layers of the system based on the multiple layer load data; sending any adjustments that should be made to throttle agents of one or more layers of the system; updating the throttling policies of one or more layers of the system based on the adjustments; and, continuing executing the business process based on the updated throttling policies of the one or more layers of the system. Another embodiment includes a non-transitory computer-readable medium storing program instructions that, when executed by one or more processors, cause one or more servers in a system to control business processes through information technology operational controls using the method.

Another embodiment of the disclosure provides a computing device for controlling business processes through information technology operational controls in a system. The computing device includes a memory storing executable instructions and one or more processors. The one or more processors are configured to execute the instructions to: receive, from each layer of multiple layers of the system, layer load data corresponding to the load at the layer associated with a business process input into the system, wherein each layer load data contains data related to a single layer of the multiple layers of the system; determining whether any adjustments should be made to one or more throttling policies corresponding to the multiple layers of the system based on the multiple layer load data; and, sending any adjustments that should be made to throttle agents of one or more layers of the system, wherein the one or more layers of the system are configured to update one or more corresponding throttling policies based on the adjustments to continue executing the business process.

DETAILED DESCRIPTION

Applications in enterprise systems may rely on multiple system handoffs between system assets in order to support a business process. Due to the complex nature of handoffs between system assets, increased insight towards controlling all of those system assets from a process end-to-end perspective is desired. Current state of the art includes (a) monitoring for individual system assets, (b) integration and business process management middleware, and (c) business controls of a single object running in a process or integration engine. None of these current approaches incorporates an end-to-end process control across the multiple disparate system assets. These current approaches have isolated control and monitoring for individual system assets, and thus exhibit inefficiencies during multiple system handoffs between system assets. Current state of the art's individual systems, business process management middleware and integration engines sometimes independently monitor their processes in their silos.

Embodiments of the disclosure provide systems and methods for information technology (IT) operational control that addresses this lack of end-to-end oversight and action by receiving monitored data from all disparate system assets, determining the most efficient overall throttling scenarios, and setting the individual system assets throttling policies to collectively achieve the optimum end-to-end throughput. Controls are external to any individual part of the end-to-end heterogeneous process; that is, controls are external to each disparate system asset. In some embodiments, throttling occurs at both the overall system level and at an interaction level in a synchronous mode.

Embodiments of the disclosure further provide systems and methods for controlling business process through IT operational controls. The method utilizes existing system assets, monitors system assets in real-time, makes appropriate throttling decisions, and sends those throttling policies to the individual system assets. Advantageously, embodiments of the disclosure provide a reduction of potential bottlenecks that would otherwise adversely affect the execution of business processes. Potential bottlenecks are detected and averted in real-time, thereby optimizing current IT system assets and greatly increasing reliability. In contrast to the current state of the art, embodiments of the disclosure offer an overall process "orchestration" across many networks, systems, applications, and entities and how these system assets will supply and consume from each other.

Figure 1:
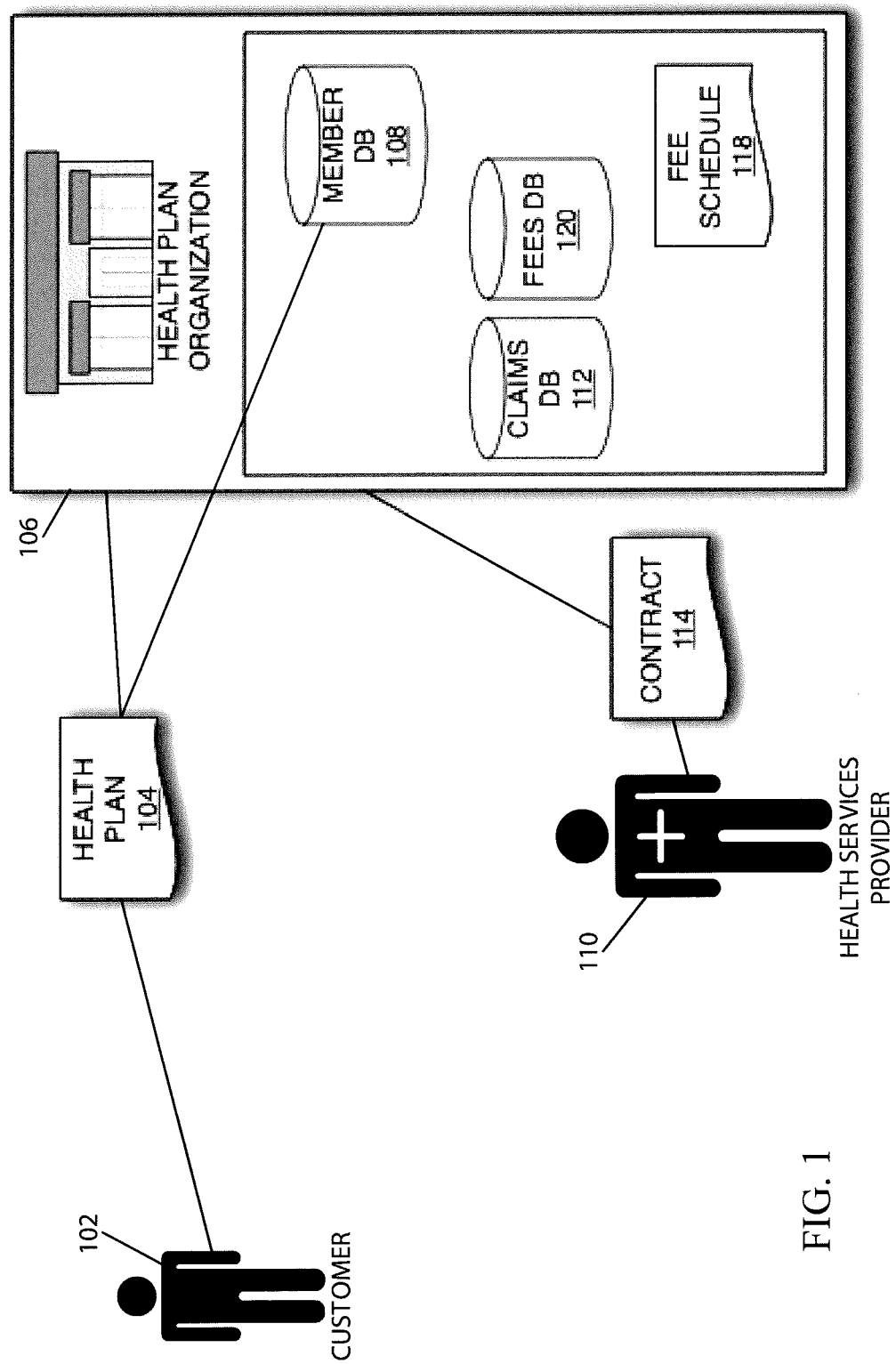
FIG. 1 is a conceptual diagram of a system with reference to an overall healthcare environment, according to one embodiment.

Turning to FIG. 1, an implementation of a system contemplated by an embodiment of the disclosure is shown with reference to an overall healthcare environment, according to one embodiment. A consumer (also referred to as a "subscriber" or "member" or "patient") 102 is a member of a health plan 104 of a health plan organization (HPO) 106. The member 102 may subscribe to the health plan 104 through, for example, his or her employer. Alternatively, the member 102 may obtain benefits of the health plan 104 through a subscriber (e.g., a spouse or child of a subscriber can be a member of a health plan). The HPO 106 can be a health insurance company and the health plan 104 can be one of a number of health insurance or related products, such as a PPO (Preferred Provider Organization), HMO (Health Maintenance Organization), POS (Point-of-Service), or the like. The health plan 104 can also be a consumer-directed health plan, such as a high deductible health plan, health reimbursement arrangement (HRA), health savings account (HSA), or the like. The member's 102 health plan 104 covers various health care services according to one of a variety of pre-arranged terms. Details for the member 102 and the corresponding plan 104 are stored in a member database 108. The terms of the plan 104 can vary greatly from plan to plan according to: what types of services are provided, where the services are provided, by whom they are provided, the extent to which the patient is personally responsible for payment, amount of deductibles, etc. Generally, however, regardless of the specific plan subscribed to, when a member 102 obtains health care services from a provider 110, either the patient 102 or the provider 110 can submit a claim to the HPO 106 for reimbursement or payment. For analysis purposes, historical claim data is stored in a claims database 112.

A health care services provider 110 may have a contractual relationship 114 with the HPO 106. Under the contract 114, the provider 110 typically agrees to provide services to members 102 of the HPO 106 at scheduled rates. The rates are stored in a fee schedule 118, preferably stored in a fees database 120 maintained by the HPO 106. By contracting with the HPO 106, the provider 110 generally increases the amount of business the provider 110 receives from members 102, and members 102 generally receive a less expensive rate than they would otherwise receive for a health service provided by the provider 110. The actual amount of out-of-pocket expense to be paid by a member 102 may vary according to the terms of his health plan 104 (e.g., co-payments, co-insurance or deductibles may apply), but will generally be at most the contracted rate.

Figure 2:
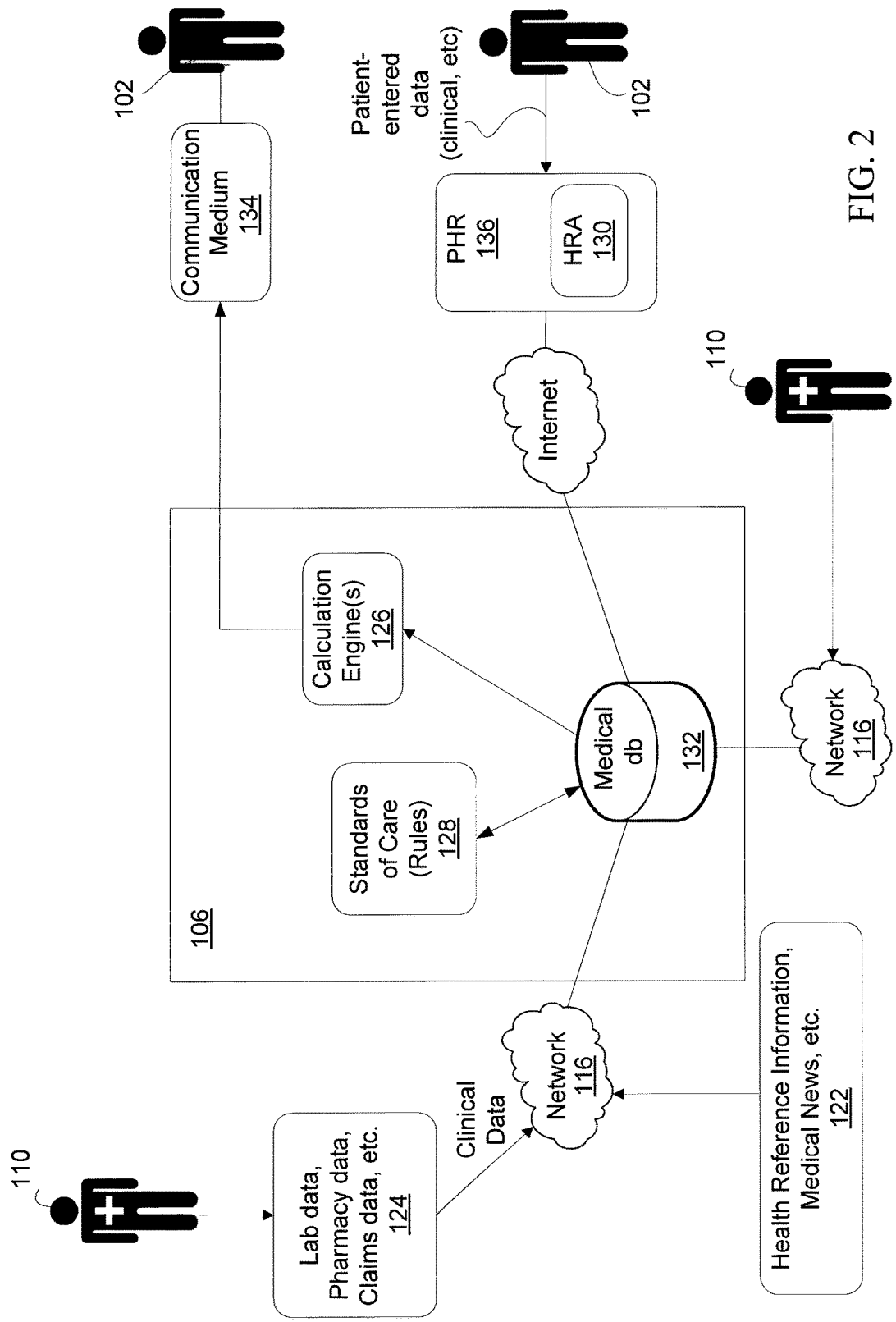
FIG. 2 is a schematic diagram illustrating an overview of a system for controlling business processes through information technology operational controls, according to one embodiment.

FIG. 2 is a schematic diagram illustrating an overview of a system for controlling business processes through information technology operational controls, according to one embodiment. A health plan organization 106 collects and processes a wide spectrum of medical care information relating to a patient 102. A personal health record (PHR) 136 of a patient 102 may be configured to solicit the patient's input for entering additional pertinent medical information, tracking follow-up actions, and allowing the health plan organization 106 to track the patient's medical history. In some embodiments, the medical care information relating to the patient can include health risk assessment (HRA) information, also referred to as a health risk appraisal, or health and well-being assessment. In one embodiment, the HRA is a questionnaire used to gather the pertinent medical information from the patient 102.

In some embodiments, when the patient 102 utilizes the services of one or more health care providers 110, a medical insurance carrier collects the associated clinical data 124 in order to administer the health insurance coverage for the patient 102. Additionally, a health care provider 110, such as a physician or nurse, can enter clinical data 124 into one or more health care provider applications pursuant to a patient-health care provider interaction during an office visit or a disease management interaction. Clinical data 124 originates from medical services claims, pharmacy data, as well as from lab results, and includes information associated with the patient-health care provider interaction, including information related to the patient's diagnosis and treatment, medical procedures, drug prescription information, in-patient information, and health care provider notes, among other things. The medical insurance carrier and the health care provider 110, in turn, provide the clinical data 124 to the health plan organization 106, via one or more networks 116, for storage in one or more medical databases 132. The medical databases 132 are administered by one or more server-based computers associated with the health plan organization 106 and comprise one or more medical data files located on a computer-readable medium, such as a hard disk drive, a CD-ROM, a tape drive, or the like. The medical databases 132 may include a commercially available database software application capable of interfacing with other applications, running on the same or different server based computer, via a structured query language (SQL). In an embodiment, the network 116 is a dedicated medical records network. Alternatively, or in addition, the network 116 includes an Internet connection that comprises all or part of the network.

In some embodiments, an on-staff team of medical professionals within the health plan organization 106 consults various sources of health reference information 122, including evidence-based preventive health data, to establish and continuously or periodically revise a set of clinical rules 128 that reflect best evidenced-based medical standards of care for a plurality of conditions. The clinical rules 128 are stored in the medical database 132.

To supplement the clinical data 124 received from the insurance carrier, the PHR 136 and/or an HRA questionnaire allow patient entry of additional pertinent medical information that is likely to be within the realm of patient's knowledge. Examples of patient-entered data include additional clinical data, such as patient's family history, use of non-prescription drugs, known allergies, unreported and/or untreated conditions (e.g., chronic low back pain, migraines, etc.), as well as results of self-administered medical tests (e.g., periodic blood pressure and/or blood sugar readings). Preferably, the PHR 136 facilitates the patient's task of creating a complete health record by automatically populating the data fields corresponding to the information derived from the medical claims, pharmacy data, and lab result-based clinical data 124. In one embodiment, patient-entered data also includes non-clinical data, such as upcoming doctor's appointments. In some embodiments, the PHR 136 gathers at least some of the patient-entered data via a health risk assessment tool (HRA) 130 that requests information regarding lifestyle, behaviors, family history, known chronic conditions (e.g., chronic back pain, migraines, etc.), and other medical data, to flag individuals at risk for one or more predetermined medical conditions (e.g., cancer, heart disease, diabetes, risk of stroke, etc.) pursuant to the processing by a calculation engine 126. Preferably, the HRA 130 presents the patient 102 with questions that are relevant to his or her medical history and currently presented conditions. The risk assessment logic branches dynamically to relevant and/or critical questions, thereby saving the patient time and providing targeted results. The data entered by the patient 102 into the HRA 130 also populates the corresponding data fields within other areas of PHR 136. The health plan organization 106 aggregates the clinical data 124 and the patient-entered data, as well as the health reference and medical news information 122, into the medical database(s) 132 for subsequent processing via the calculation engine 126.

The health plan organization 106 includes a multi-dimensional analytical software application including a calculation engine 126 comprising computer-readable instructions for performing analysis on the contents of the medical databases 132. The calculation engine 126 may include one or more servers in an enterprise environment for performing the analysis on the contents of the medical databases 132. System asset allocation in the server(s) and related networked systems including the medical databases 132 may employ end-to-end throttling according to embodiments of the disclosure. For example, when the calculation engine 126 performs analysis on the contents of the medical databases 132 and detects an increase in file access to a specific file, the server(s) may employ file splitting to allow multiple access to the contents of the specific file. In other implementations, the server(s) may also adjust network traffic to accommodate the multiple access. Using embodiments of the disclosure, the calculation engine 126 can make these two adjustments at the same time, once the increase in file access to the specific file is detected, instead of waiting for one event to trigger the next.

In some embodiments, referring to FIG. 2, a patient may be stratified into risk tiers, including a high risk tier, a moderate risk tier, and a low risk tier. Based on the risk tier of a patient and other "engagement factors," as described in greater detail herein, the health plan organization can reach out to the patient 102 via communications medium 134. Example communications media 134 include telephone, postal mail, email, text message, or other electronic or non-electronic communication media. In various embodiments, the type of communication medium 134 used to reach out to or "engage" the patient 102 depends on the risk tier and/or other engagement factors.

While the entity relationships described above are representative, those skilled in the art will realize that alternate arrangements are possible. In one embodiment, for example, the health plan organization 106 and the medical insurance carrier are the same entity. Alternatively, the health plan organization 106 is an independent service provider engaged in collecting, aggregating, and processing medical care data from a plurality of sources to provide a personal health record (PHR) service for one or more medical insurance carriers. In yet another embodiment, the health plan organization 106 provides PHR services to one or more employers by collecting data from one or more medical insurance carriers.

Figure 3:
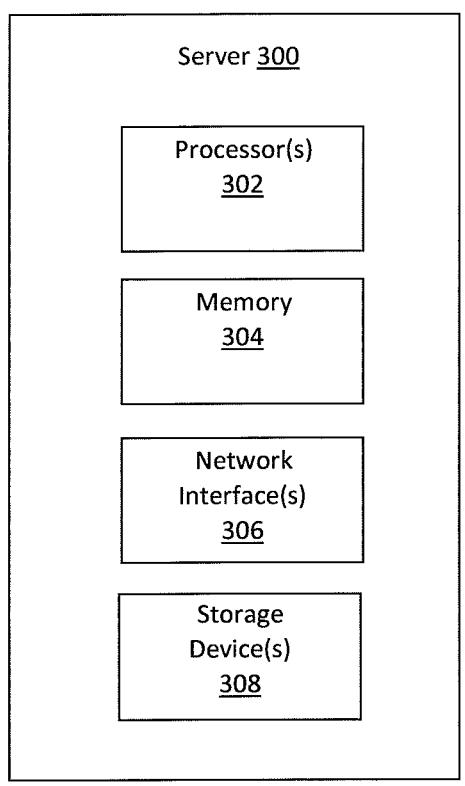
FIG. 3 is a block diagram illustrating components for a server from the system illustrated in FIG. 1 according to one embodiment.

Turning to FIG. 3, a block diagram is shown illustrating components for a server 300, according to certain aspects of the disclosure. For example, server 300 may be a server-based computer associated with the health plan organization 106 in FIGS. 1-2.

Server 300 includes one or more processors 302, memory 304, network interface(s) 306, storage device(s) 308, and software modules stored in memory 304. The software modules are provided as being stored in memory 304, but in certain embodiments, the software modules are stored in storage devices 308 or a combination of memory 304 and storage devices 308. In certain embodiments, each of the components including the processor(s) 302, memory 304, network interface(s) 306, storage device(s) 308, media manager 310, connection service router 312, data organizer 314, and database editor 316 are interconnected physically, communicatively, and/or operatively for inter-component communications.

Processor(s) 302, analogous to processor(s) 202 in client device 104, is configured to implement functionality and/or process instructions for execution within the server 300. For example, processor(s) 302 executes instructions stored in memory 304 or instructions stored on storage devices 308. Memory 304, which may be a non-transient, computer-readable storage medium, is configured to store information within server 300 during operation. In some embodiments, memory 304 includes a temporary memory, i.e., an area for information not to be maintained when the server 300 is turned off. Examples of such temporary memory include volatile memories such as random access memories (RAM), dynamic random access memories (DRAM), and static random access memories (SRAM). Memory 304 also maintains program instructions for execution by processor(s) 302. The server 300, although shown as including a processor(s) 302 and memory 304, may further include a microprocessor, microcontroller and/or dedicated circuitry.

Server 300 uses network interface(s) 306 to communicate with external devices via one or more networks depicted as network 108 and network 112 in FIG. 1. Such networks may also include one or more wireless networks, wired networks, fiber optics networks, and other types of networks through which communication between the server 300 and an external device may be established. Network interface(s) 306 may be a network interface card, such as an Ethernet card, an optical transceiver, a radio frequency transceiver, or any other type of device that can send and receive information.

Storage devices 308 in server 300 also include one or more non-transient computer-readable storage media. Storage devices 308 are generally configured to store larger amounts of information than memory 304. Storage devices 308 may further be configured for long-term storage of information. In some examples, storage devices 304 include non-volatile storage elements. Non-limiting examples of non-volatile storage elements include magnetic hard discs, optical discs, floppy discs, flash memories, resistive memories, or forms of electrically programmable memories (EPROM) or electrically erasable and programmable (EEPROM) memories.

Figure 4:
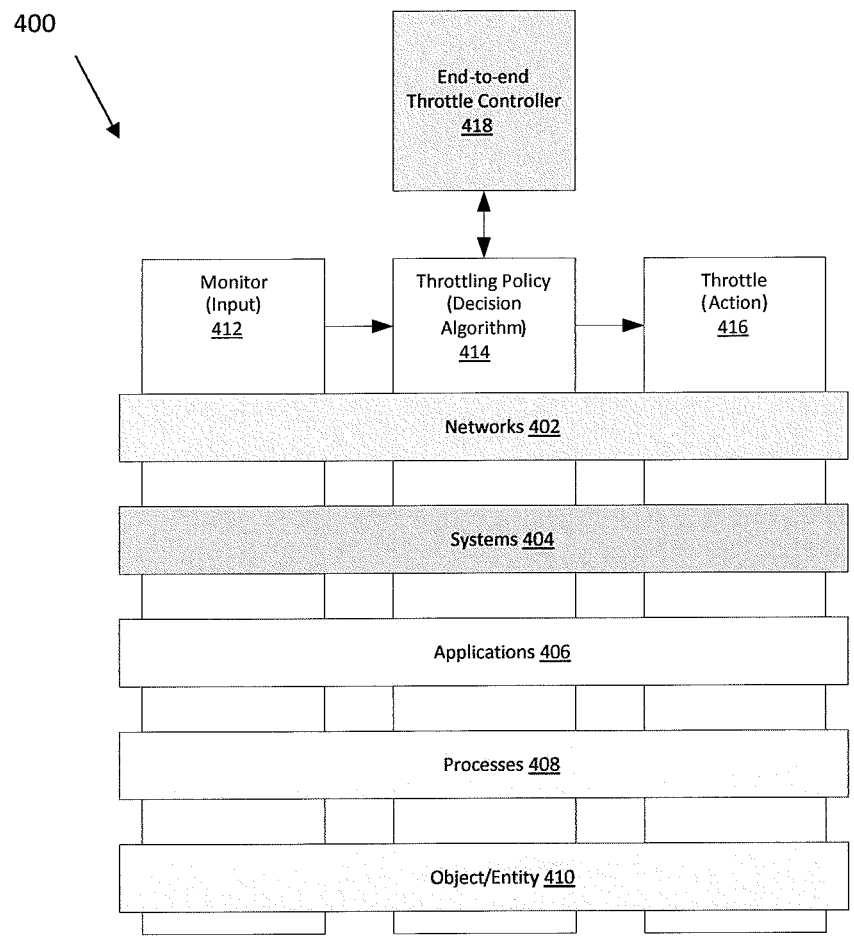
FIG. 4 is a block diagram illustrating a system for controlling business processes through information technology operational controls, according to one embodiment.

FIG. 4 is a block diagram illustrating a system 400 for controlling business processes through information technology operational controls, according to one embodiment. As shown, the system includes multiple layers, including networks layer 402, systems layer 404, applications layer 406, processes layer 408, and object/entity layer 410. The layers 402, 404, 406, 408, 410 shown in FIG. 4 are merely examples, and other or different layers be included in other systems that implement embodiments of the disclosure. Each of the layers 402, 404, 406, 408, 410 has its own independent monitor component 412, throttling policy component 414, and throttle components 416.

Each independent monitor component 412 detects the "health" of its own associated system asset layer. Health, in one implementation, refers to levels of control associated with the business processes controls. For example, health may refer to whether "is data flowing at a proper pace through and to the next supplier?", "is the detection processing flow working?", etc. Each independent throttling policy component 414 determines what throttling action should take place based on the monitored input and the policy that is in place for that associated system asset layer. Each independent throttle component 416 makes the appropriate adjustments to the associated system asset layer.

The system 400 also includes an end-to-end throttle controller 418 that communicates with each of the independent throttling policy components 414 from each layer to get a collective view of the health of all the layers from end-to-end. Based on the input from the independent throttling policy components 414, the end-to-end throttle controller 418 determines what, if any, independent throttling action needs to take place and at which layer, and will send the new throttling policy to the appropriate throttling policy component 414, thereby changing the appropriate action taken by the independent throttle components 416. The end-to-end throttle controller 418 has an end-to-end throttling control across all layers that were not previously possible in conventional approaches. Each of the independent monitor components 412, the independent throttling policy components 414, the independent throttle components 416, and the end-to-end throttle controller 418 may be implemented as software instructions stored in a memory and executed by a processor, such as the memory 304 and processor 302 in FIG. 3.

As such, embodiments of the disclosure provide systems and methods by which the various layers of IT assets can be monitored and controlled/throttled in such a way as to optimize each layer with the overall goal of moving a business process from end-to-end efficiently as possible. Embodiments of the disclosure provide a communication and controlling system configured to set an end-to-end process throttling policy, decompose the throttling policy to constituent parts applying to each part of the end-to-end process, enforce a current throttling policy, and optimize the current throttling policy through end-to-end monitoring feedback.

In some embodiments, throttling the intake to the business process may include: application programming interface (API) traffic management, holding a file, or file splitting (e.g., for additional parallelism, to speed up throughput). In some embodiments, throttling cross-domain connection/integration points may include: API traffic management, service traffic management, holding a file, or file splitting. Each layer has the ability to throttle itself, or parts of itself. In some embodiments, the enterprise system with end-to-end monitoring and control can be optimized continuously via machine learning, for example, utilizing predictive analytical insight or predictive analytics to recognize choke patterns, affect adjustments to one or more layers, and to set policies for maximum throughput and zero "outage." Machine leaning applied to the enterprise system with end-to-end monitoring and control provides the ability to make predictions on data through patterns of use, historical references and other factors. Using machine learning the enterprise system may continuously track and monitor the data being passed, taking into account data properties such as payload size, frequency, expected from monitored data activity, and timing of the arrival of the monitored data. The enterprise system continuously monitors the input, throughput and output and based on patterns of use and adjusts or throttles the throughput based on machine ability and past experiences (historical information).

Figure 5:
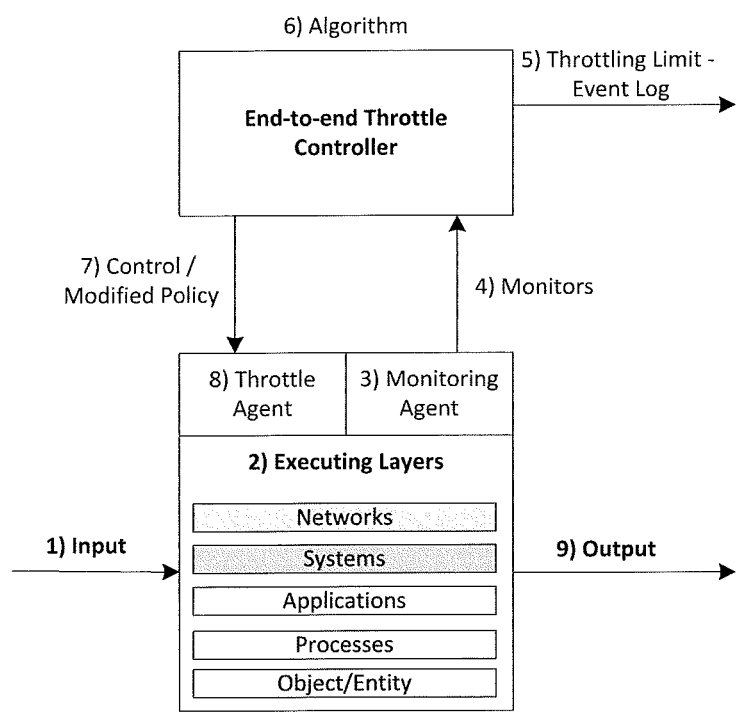
FIG. 5 is a block diagram illustrating a process flow for controlling business processes through information technology operational controls, according to one embodiment.

FIG. 5 is a block diagram illustrating a process flow for controlling business processes through information technology (IT) operational controls, according to one embodiment. FIG. 5 illustrates an example method by which the various layers of IT assets can be monitored and controlled/throttled in such a way as to optimize each layer with the overall goal of moving a business process from end-to-end with the as efficiently as possible. In the example shown in FIG. 5, the process flow includes Steps numbered 1-9, including:

1. Input a business process
2. Execute business process on appropriate layers
3. Monitoring agents capture individual layer data to be forwarded on
4. Monitored data is received by end-to-end throttle controller
5. Any data that is outside of the throttling limits will be sent to an event log
6. An algorithm is used to assess the monitored data and determine if any adjustments need to be made
7. When adjustments are necessary, those adjustments are sent to the appropriate throttle agent in terms of a policy
8. The throttle agent will take the appropriate action to the identified layer
9. The business process will continue moving through the necessary layers until its execution is completed and an output is generated or viewed Each step identified above is described in more detail. At step 1, the business process is received at one or more servers at the health plan organization 106; that is, the executing layers intake the business process. At step 1, received data volume and response time is monitored and controlled at the one or more servers at the health plan organization 106. The server(s) determines which layers in the executing layers are invoked based on the requirements of the received business process.

At step 2, the business process is executed on the appropriate layers. At the beginning of step 2, the server(s) begins executing the business process input at step 1 on various layers. While the execution is ongoing, system attributes are being monitored by monitoring agents associated with each layer. In some embodiments, depending on the business process being executed, some layers execute before other layers. That is, the results from a preceding layer is required for proper execution in the next layer, so during execution, the some required layers may be dormant waiting for other layers to finish executing.

At step 3, monitoring agents capture individual layer data. This step is identified separately from step 2, but can occur simultaneously. Monitoring agents collect monitored data in local logs, using logic to determine relevant data. Relevant monitored data is forwarded on to the end-to-end throttle controller.

At step 4, the monitored data is received by the end-to-end throttle controller. The incoming monitored data triggers the end-to-end throttle controller to accept the monitored data. The monitored data is then parsed by the end-to-end throttle controller for consistency.

At step 5, the end-to-end throttle controller sends any data that is outside of throttling limits to an event log. The end-to-end throttle controller also determines at this step the impact of the data to the overall end-to-end importance. That is, it determines the impact of the data to the overall efficiency of executing the business process from start to finish.

At step 6, the end-to-end throttle controller runs an algorithm to assess all the monitored data and determine if any adjustments need to be made. When adjustments are necessary, the adjustments are generated by the end-to-end throttle controller.

At step 7, the adjustments generated are sent by the end-to-end throttle controller to appropriate throttle agents as updated policies.

At step 8, throttle agents that receive the updated policies will take appropriate actions at their respective layers. The prescribed action of the updated policies scripts are executed for local throttle, that is, at a per layer basis.

At step 9, the business process continues moving through the necessary layers until completion. Steps 3 through 8 occur independent of step 9. Step 9 is analogous to step 2. Step 2 was described using the previous policy, while step 9 continues execution of the business process with updated policies due to actions undertaken by the throttle agents at step 8. If no action is taken by the throttle agents due to no change in policy, then step 9 is identical to step 2.

Figure 6:
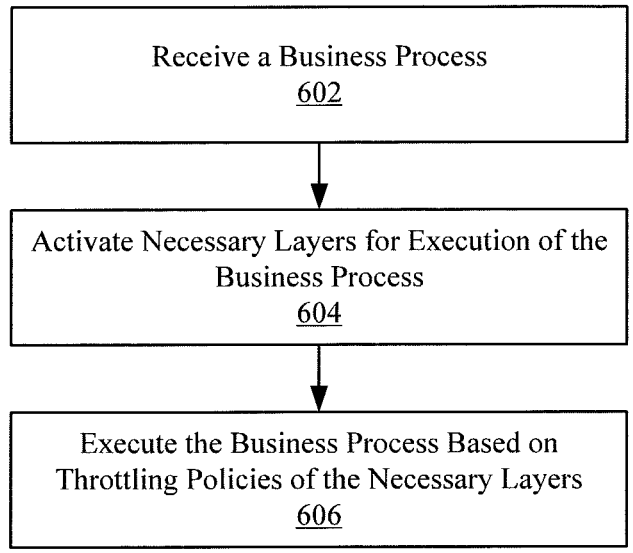
FIG. 6 is a flow diagram illustrating tasks performed at executing layers of FIG. 5, according to one embodiment.

FIG. 6 is a flow diagram illustrating tasks performed at executing layers of FIG. 5, according to one embodiment. At stage 602, one or more servers at the health plan organization 106 receive a business process at one or more executing layers. Examples of executing layers are provided, for example, in FIG. 4 and FIG. 5 and may include networks 402, system 404, applications 406, processes 408, and object/entity 410. At stage 604, the servers determine which executing layers are necessary for executing the business process and activate the necessary layers. At stage 606, the executing layers run the business process based on throttling policies of the necessary layers.

Figure 7:
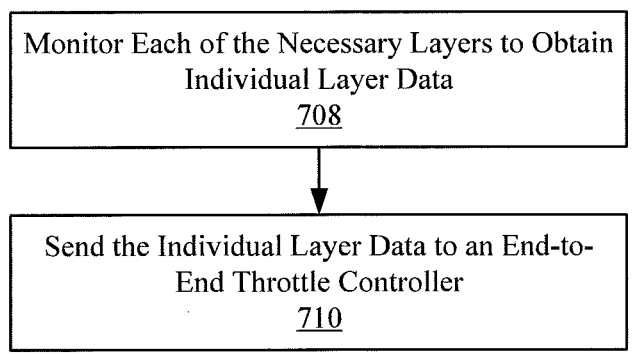
FIG. 7 is a flow diagram illustrating tasks performed by a monitoring agent, according to one embodiment.

FIG. 7 is a flow diagram illustrating tasks performed by a monitoring agent, according to one embodiment. A monitoring agent is depicted graphically as monitor component 412 in FIG. 4 and as monitoring agent in FIG. 5. At stage 708, the monitoring agent observes execution of the business process at each of the necessary layers of stage 604 to obtain individual layer data. Individual layer data includes, for example, specific data about the networks involved, specific data about the systems being used, specific data about the applications that are invoked, etc. Individual layer data may also include data required for throttling input/output, for example, individual layer data may answer the questions, "Is the supplying or consuming network available?", "What is the integrity of the supplying or consuming network?", "What is the supplying network speed compared to the consuming network speed?", etc. The throttling controller may make throttling adjustments based on answers to these questions. At stage 710, the monitoring agent sends the individual layer data to an end-to-end throttle controller.

Figure 8:
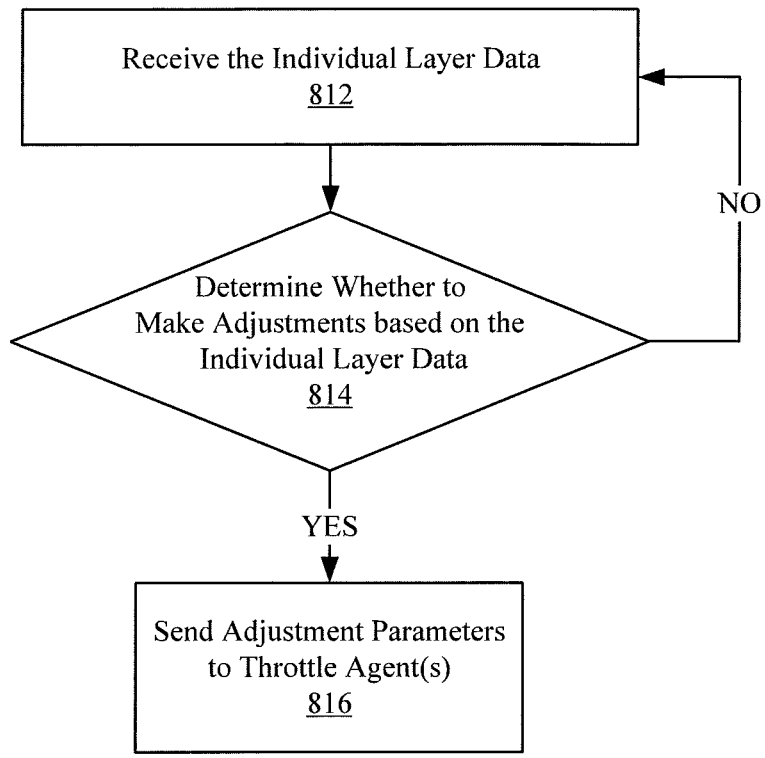
FIG. 8 is a flow diagram illustrating tasks performed at an end-to-end throttle controller, according to one embodiment.

FIG. 8 is a flow diagram illustrating tasks performed at an end-to-end throttle controller, according to one embodiment. An end-to-end throttle controller is shown in FIG. 4 as end-to-end throttle controller 418. At stage 812, the end-to-end throttle controller receives the individual layer data from the monitoring agent. At stage 814, the end-to-end throttle controller determines whether to make adjustments based on the individual layer data. If no adjustments are necessary, then the end-to-end throttle controller continues receiving individual layer data from monitoring agents. If adjustments are necessary, then at stage 816, the end-to-end throttle controller sends adjustment parameters to one or more throttle agents. The adjustment parameters sent at stage 816 are computed by the end-to-end throttle controller using an algorithm. Individual layer data may also include data required for throttling input/output, for example, individual layer data may answer the questions, "Is the supplying or consuming network available?", "What is the integrity of the supplying or consuming network?", "What is the supplying network speed compared to the consuming network speed?", etc. The throttling controller may make throttling adjustments based on answers to these questions.

Figure 9:
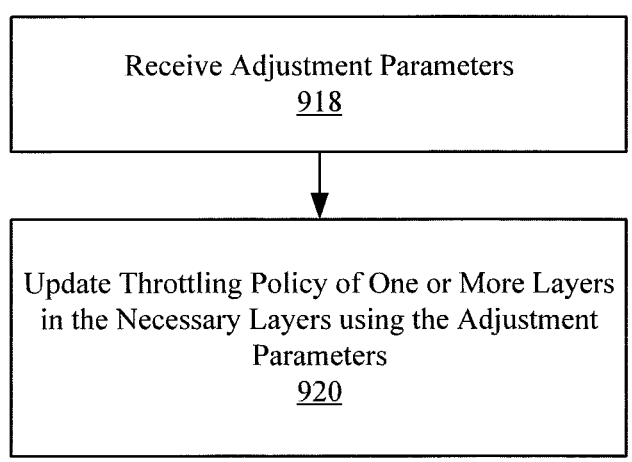
FIG. 9 is a flow diagram illustrating tasks performed at a throttle agent, according to one embodiment.

FIG. 9 is a flow diagram illustrating tasks performed at a throttle agent, according to one embodiment. At stage 918, the throttle agent receives the adjustment parameters sent by the end-to-end throttle controllers. At stage 920, the throttle agent updates the throttling policy of its respective layer using the adjustment parameters.

Figure 10:
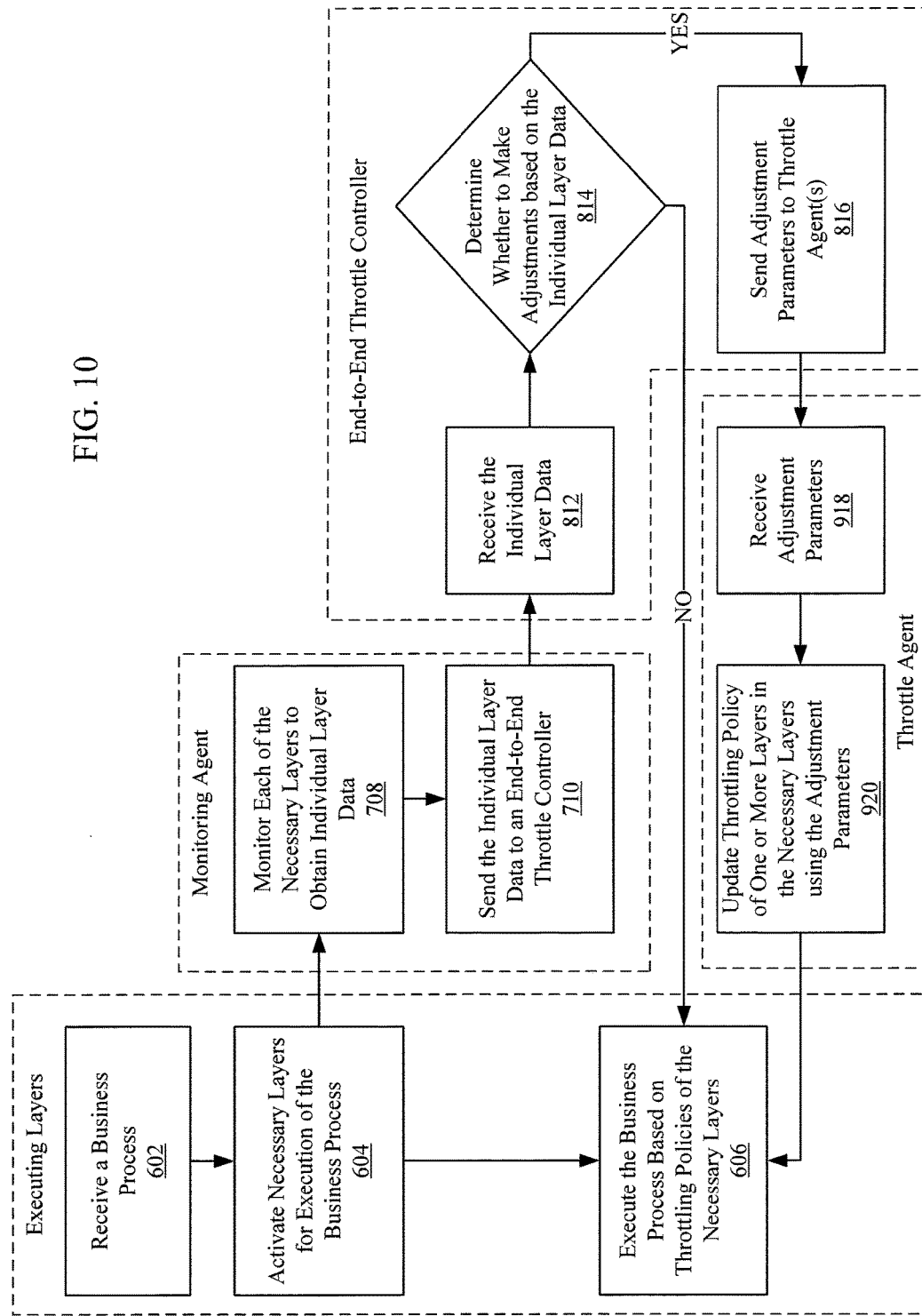
FIG. 10 is a flow diagram for controlling business processes through information technology operational controls, according to one embodiment of the disclosure.

FIG. 10 is a flow diagram for controlling business processes through information technology operational controls, according to one embodiment of the disclosure. FIG. 10 illustrates one embodiment of how the flow diagrams of FIGS. 6-9 may be combined to control the execution of a business process. At stage 602, one or more servers at the health plan organization 106 receives the business process, and at stage 604, necessary layers in the executing layers of the servers are activated for execution of the business process.

In some embodiments, when the business process is received and the necessary layers of the executing layers are activated, monitoring agents associated with each necessary layer begin obtaining individual layer data at stage 708. For example, some layers may be in the process of executing a previous business process, so when the business process is received at the servers and the necessary layers identified, the monitoring agents note the increase in data processing anticipated at each of the necessary layers due to input data volume of the business process.

At stage 606, the executing layers execute the business process based on current throttling policies of the necessary layers. As the business process is being executed, the monitoring agents of each layer sends individual layer data to an end-to-end throttle controller at stage 710.

At stage 812, the end-to-end throttle controller receives the individual layer data, and at stage 814, determines whether to make adjustments based on the individual layer data. When no adjustment is necessary based on the individual layer data received, then the executing layers continue executing the business process based on current throttling policies of the necessary layers at stage 606. When adjustments are necessary, at stage 816, the end-to-end throttle controller determines the adjustments and sends adjustment parameters to throttle agents in executing layers requiring adjustment.

At stage 918, the throttle agents requiring adjustments receive adjustment parameters from the end-to-end throttle controller. At step 920, the throttle agents update the current throttling policy using the adjustment parameters. Then at stage 606, the executing layers continue executing the business process but with the updated throttling policies of stage 920.

EXAMPLE

Figure 11:
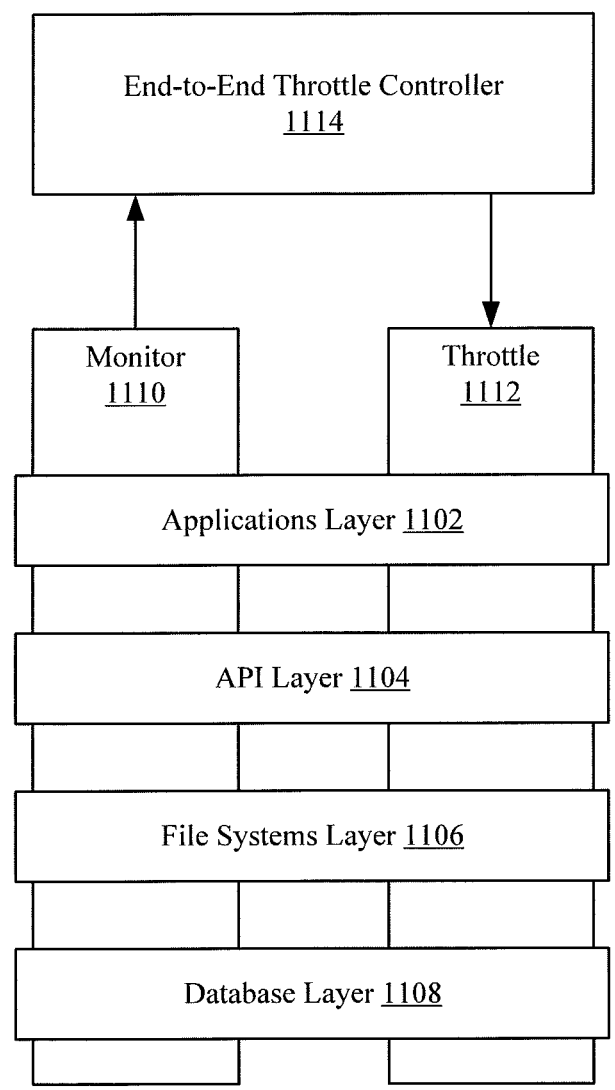
FIG. 11 is an example of controlling business processes through information technology operational controls, according to one embodiment.

FIG. 11 provides a working example of embodiments for controlling business processes through information technology operational controls. In this example, the processing system includes the following components: an end-to-end throttle controller 1114, an application layer 1102, an API or services layer 1104, a file systems layer 1106, and a database layer 1108. Each layer has its own individual monitoring component 1110 and individual throttling policy system with throttle component 1112.

The application layer 1102 monitors the amount of users that have started up a new application. The throttling policy system for the application layer 1102 controls how many virtual machine instances need to be created based on the load. The load may be defined as the amount of running applications, number of virtual machines running, amount of processing resources used, amount of memory being used, or any other metric that corresponds to use of computing resources. For example, in the application layer 1102, the throttling agent will have gathered application throughput capabilities and processing speed and effect control over the flow of data based on the end-to-end throttle controller 1114. The controller may request a single application instance to run or multiple application instances to run to satisfy the calculated demands.

API (services) layer 1104 monitors the amount of API usage based on present interactions between applications and backend systems. The throttling policy system for the API layer 1104 controls how many instances of the APIs need to be created based the load (i.e., the amount of API/service calls that are invoked).

The file system layer 1106 monitors the amount or traffic flow of files based on present usage being invoked by some APIs or services. The throttling policy system for the file system layer 1106 controls some file splitting to optimize consumption based on the performance of the file consumption.

The database layer 1108 monitors the amount of data being written to the database being invoked by the process of storing the data from the files that are being consumed. The throttling policy system for the database layer 1108 controls the amount of database segments needed to handle the load based on the files data input for storage.

In some embodiments, each of the throttling policies for the various layers can increase performance at a resource cost and needs to be controlled for optimal performance versus operational cost. Also, each one of the throttling policies takes a certain amount of time to actually make the physical change to the layers (i.e., there may be a lag or delay with any configuration change).

Embodiments of the disclosure will be applied to the example in FIG. 11 to describe events that take place during an "Open Enrollment for Healthcare benefits" period. Typically, the "Open Enrollment" period takes place once a year with a time constraint window for customers to enroll, which causes a unpredictable increase in IT system resources usage. Two Scenarios will be presented, the first showcasing a conventional approach where no end-to-end throttling controller is present, and the second showcasing an embodiment where an end-to-end throttling is realized.

Scenario 1: Conventional Approach (No End-to-End Throttling Controller)

Continuing with the example, in a conventional system, an Open Enrollment period opens to the public on Monday morning and many thousands of customers log in to the Open Enrollment application, interfacing with enterprise systems of a health plan organization. Assuming the conventional health plan organization's enterprise system has executing layers as depicted in FIG. 11, the Open Enrollment event causes a very large amount of the Open Enrollment applications to be monitored by the application layer 1102. When the application layer 1102 detects a large number of customers requesting to run the Open Enrollment application, the throttling policy of the application layer 1102 gets changed to create more virtual machine instances to handle the increased load.

As all of these new Open Enrollment applications start utilizing the API (services), the API layer's monitor notices an increase in the use of API (services) and hence the API layer's throttling policy is changed to create more instances of the APIs. When changing the policy to adapt to the increased utilization of the APIs, there is a delay in reaction. That is, the new throttling policy takes time to be realized; there is a finite time delay or time resource the enterprise system must expend to create more instances of the APIs.

As all of these new APIs start invoking file creation and transportation, the monitor of the file systems layer notices the increased load. This increase in file creation and transportation causes the throttling policy of the file systems layer 1106 to be updated, by for example, starting to split the files—however, there is a delay in reaction here also.

As all of these new files created are being sent to the database for consumption/storage, the monitor of the database layer 1108 notices the increased load, and the throttling policy of the database layer 1108 gets changed to create more segments—however, there is once again a delay in reaction here.

In such a conventional system, when each layer gets increased usage or determines that there is a normative or expected increase in load, each individual layer monitors and changes its respective throttling policy as needed and, more than often, reacts in sufficient time. Unfortunately, when there is an unpredictable increase in usage, the delay gets compounded at each layer and overall system reliability and availability are severely degraded and the customers get terrible response or none at all. The propagated delay from each layer compounds the total delay, making the enterprise system inefficient.

Scenario 2: Embodiments of the Disclosure (with End-to-End Throttling Controller)

Still referring to the example in FIG. 11, when incorporating embodiments of the disclosure, Open Enrollment opens to the public on Monday morning and many thousands of customers login to the Open Enrollment application, interfacing with enterprise systems of a health plan organization. Assuming the health plan organization's enterprise system has executing layers as depicted in FIG. 11, the Open Enrollment event causes a very large amount of Open Enrollment applications to be monitored at the application layer 1102. When the monitor of application layer 1102 detects a large number of customers requesting to run the Open Enrollment application, the throttling policy of the application layer 1102 gets changed to create more virtual machine instances to handle the increased load.

The change in the throttling policy of the application layer 1102 along with other information, for example, performance results (response times, volume counts, thresholds, service level agreements, etc.) is transmitted to the end-to-end throttling controller 1114 in the individual layer data of the application layer 1102. The end-to-end throttling controller 1114 then becomes aware of the policy change in the application layer and other information by reading the individual layer data from the monitor of the application layer 1102. The end-to-end throttling controller 1114 recognizes the unpredictable increase in application usage and checks the other monitoring information for the other layers. The end-to-end throttling controller 1114 notices that the throttling policies of other layers have not reacted appropriately, that is, the other layers are not ready for the increased load.

The end-to-end throttling controller 1114 then makes some calculations based on the increased application usage and determines new throttling policies for the other layers that can handle this new load. The end-to-end throttling controller distributes the new throttling policies to the throttle agents of the other involved layers and each respective layer makes the appropriate changes. As such, all the remaining layers have been pre-configured to handle the unpredictable load and have now coordinated increase in capacity. Therefore, in this scenario using some embodiments of the disclosure, all the new applications can utilize: (1) all the new APIs created as a response to a change in policy in the application layer 1102, (2) all the new file splitting as a response to a change in policy in the application layer 1102, and (3) all the new database segments as a response to a change in policy in the application layer 1102. Since all subsequent layers are adjusted/throttled based on a change in policy in the application layer 1102, the enterprise system will respond quicker in the Open Enrollment scenario, achieving virtually no delay in reaction time.

This scenario is juxtaposed with the conventional scenario where a chain of "policy change" and "react to policy change" adds processing delay. Using embodiments of the disclosure, since the API layer 1104, file systems layer 1106, and database layer 1108 had their throttling policies changed by the end-to-end throttling controller 1114 once the end-to-end throttling controller 1114 noticed an unpredictable increase in application usage, all the appropriate layers were adjusted and ready for this new increased load ahead of time and before subsequent delays were encountered. Once the application load changes again, the end-to-end throttling controller reassess the new throttling policies for each layer and redistribute them accordingly. In scenario 2, the change in throttling policy of application layer 1102 was communicated to the end-to-end throttling controller 1114 which then changed the throttling policies of the downstream layers. This shows that each layer is independent of the end-to-end throttling controller 1114 and can change its throttling policy. The end-to-end throttling controller 1114 is then tasked to respond to how that change may affect downstream layers in order to reduce processing delay.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for controlling business processes through information technology operational controls, the method performed by one or more servers, each server in the one or more servers including one or more processors, the method comprising:
   receiving a business process for execution by a plurality of layers;
   monitoring, via one or more monitoring agents, a load at each layer of the plurality of layers;
   sending, by a monitoring agent associated with a first layer to an end-to-end throttle controller, layer load data corresponding to the load at the first layer;
   receiving, from the end-to-end throttle controller, adjustments for one or more throttling policies at throttle agents for one or more layers of the plurality of layers;
   updating the one or more throttling policies of the one or more layers based on the adjustments to generate updated throttling policies; and
   executing the business process based on the updated throttling policies of the one or more layers.

2. The method according to claim 1, wherein the plurality of layers comprise one or more selected from the group consisting of: a network layer, a systems layer, an applications layer, a processes layer, and an object layer.

3. The method according to claim 1, wherein the updating the throttling policies of the one or more layers comprises performing one or more tasks selected from the group consisting of: creating additional virtual machines, file splitting, holding a file, performing application programming interface (API) traffic management, and performing service traffic management.

4. The method according to claim 1, wherein the layer load data for the first layer comprises a change in a throttling policy of the first layer.

5. The method according to claim 1, further comprising:
activating necessary layers from the plurality of layers, wherein the monitoring the load involves monitoring the load at the necessary layers.

6. The method according to claim 1, wherein the load for a particular layer comprises one or more selected from the group consisting of: application requests, application programming interface (API) traffic, and database traffic.

7. The method according to claim 1, wherein the business process is received by a first server that implements at least a portion of the layers in the plurality of layers, and wherein the end-to-end throttle controller is implemented by a second server in communication with the monitoring agents via a network.

8. A non-transitory computer-readable medium storing program instructions that, when executed by one or more processors included in one or more servers, control business processes through information technology operational controls, by performing the steps of:
receiving a business process for execution by a plurality of layers;
monitoring, via one or more monitoring agents, a load at each layer of the plurality of layers;
sending, by a monitoring agent associated with a first layer and to an end-to-end throttle controller, layer load data corresponding to the load at the first layer;
receiving, from the end-to-end throttle controller, adjustments for one or more throttling policies at throttle agents for one or more layers of the plurality of layers;
updating the one or more throttling policies of the one or more layers based on the adjustments to generate updated throttling policies; and
executing the business process based on the updated throttling policies of the one or more layers.

9. The computer-readable medium according to claim 8, wherein the plurality of layers comprise one or more selected from the group consisting of: a network layer, a systems layer, an applications layer, a processes layer, and an object layer.

10. The computer-readable medium according to claim 8, wherein the updating the throttling policies of the one or more layers comprises performing one or more tasks selected from the group consisting of: creating additional virtual machines, file splitting, holding a file, performing application programming interface (API) traffic management, and performing service traffic management.

11. The computer-readable medium according to claim 8, wherein the layer load data for the first layer comprises a change in a throttling policy of the first layer.

12. The computer-readable medium according to claim 8, further comprising:
activating necessary layers from the plurality of layers, wherein the monitoring the load involves monitoring the load at the necessary layers.

13. The computer-readable medium according to claim 8, wherein the load for a particular layer comprises one or more selected from the group consisting of: application requests, application programming interface (API) traffic, and database traffic.

14. The computer-readable medium according to claim 8, wherein the business process is received by a first server that implements at least a portion of the layers in the plurality of layers, and wherein the end-to-end throttle controller is implemented by a second server in communication with the monitoring agents via a network.

15. A computing device for controlling business processes through information technology operational controls, the computing device comprising:
a memory storing executable instructions; and
one or more processors configured to execute the instructions to:
receive, from monitoring agents for each layer of a plurality of layers implemented by one or more servers configured to execute a business process, layer load data corresponding to the load at a first layer;
determine adjustments to one or more throttling policies corresponding to one or more layers in the plurality of layers based on the layer load data corresponding to the load at the first layer;
send adjustments for one or more throttling policies to throttle agents corresponding to the one or more layers, wherein the one or more throttling policies are updated by the throttle agents based on the adjustments.

16. The computing device according to claim 15, wherein the plurality of layers comprise one or more selected from the group consisting of: a network layer, a systems layer, an applications layer, a processes layer, and an object layer.

17. The computing device according to claim 15, wherein the updating the throttling policies of the one or more layers comprises performing one or more tasks selected from the group consisting of: creating additional virtual machines, file splitting, holding a file, performing application programming interface (API) traffic management, and performing service traffic management.

18. The computing device according to claim 15, wherein the layer load data for the first layer comprises a change in a throttling policy of the first layer.

19. The computing device according to claim 15, wherein the load for a particular layer comprises one or more selected from the group consisting of: application requests, application programming interface (API) traffic, and database traffic.

20. The computing device according to claim 15, wherein the business process is received by a first server that implements at least a portion of the layers in the plurality of layers configured to execute the business process, and wherein the end-to-end throttle controller is implemented by a second server in communication with the monitoring agents via a network.

* * * * *